United States Patent [19]

Kamijo et al.

[11] Patent Number: 5,602,165
[45] Date of Patent: Feb. 11, 1997

[54] TRANSDERMAL ABSORPTIVE DRUG FORMULATION

[75] Inventors: Shinji Kamijo, Tokyo; Jun Imai, Kanagawa-ken; Hiromichi Kodaira, Tochigi-ken, all of Japan

[73] Assignee: Kyorin Seiyaku Kabushiki Kaisha, Tokyo, Japan

[21] Appl. No.: 240,962

[22] Filed: May 10, 1994

Related U.S. Application Data

[63] Continuation of Ser. No. 97,319, Jul. 26, 1993, abandoned, which is a continuation of Ser. No. 283,246, Dec. 12, 1988, abandoned.

[30] Foreign Application Priority Data

Dec. 10, 1987  [JP]  Japan .................. 62-312593

[51] Int. Cl.$^6$ .............................................. A61K 31/415
[52] U.S. Cl. ............................... 514/406; 514/403
[58] Field of Search ........................ 514/406, 413, 514/403, 419

[56] References Cited

U.S. PATENT DOCUMENTS 4,568,343  2/1986  Leeper et al. .......................... 514/552
5,164,189  5/1991  Farhadieh et al. ..................... 424/448

FOREIGN PATENT DOCUMENTS 0118916   9/1984   European Pat. Off. .
0156243  10/1985   European Pat. Off. .
0215438   3/1987   European Pat. Off. .
2182914  12/1973   France .

OTHER PUBLICATIONS

Chem Abst, 106:436d (1987), Yoshitaka et al.
Chem Abst, 109:98852w (1988), Zupan et al.
Chem Abst, 105:18189q (1986), Sato et al.
Chem Abst, 109:215909h (1988), Bannon et al.
Chemical Abstracts, vol. 103, No. 9, 2nd Sep. 1985 p. 40, No. 64597c, Columbus Ohio, US;.
Y. Kudo et al Effect of KC–404 on experimental cerebral infarction in rats & Nippon Yakurigaku Zasshi 1985 (85(6), 435–41.

*Primary Examiner*—Zohreh Fay
*Attorney, Agent, or Firm*—McAulay Fisher Nissen Goldberg & Kiel, LLP

[57] ABSTRACT

A transdermal absorptive drug formulation containing 3-isobutyryl-2-isopropylpyrazolo [1,5-a]pyridine as active ingredient effective for bronchial asthma and cerebrovascular disorder is provided. The formulation affords excellent sustained releasing and long acting characteristics with substantially reduced side-effects such as nausea and vomitting.

10 Claims, No Drawings

TRANSDERMAL ABSORPTIVE DRUG FORMULATION

This is a continuation of application Ser. No. 08/097,319, filed Jul. 26, 1993, now abandoned which, in turn, is a continuation of application Ser. No. 07/283,246, filed Dec. 12, 1988, now abandoned.

BACKGROUND OF THE INVENTION

1. Field of the Invention

This invention relates to a transdermal absorptive drug formulation containing 3-isobutyryl-2isopropylpyrazolo-[1,5-a]pyridine ( hereinafter referred to as ibudilast according to its international nonproprietary name) which is an improving drug for bronchial asthma and cerebrovascular disorder.

2. Description of the Related Art

Ibudilast is well known as a chemical compound developed by Irikura et al. (Japanese Patent Publication Sho 52-29318, corresponding to U.S. Pat. No. 3,850,941, U.K. Patent 1,378,375 and so on) and has been proved by clinical tests to be useful for preventing and treating bronchial asthma, and still more its utility as an improved drug for cerebrovascular disorder has been reported. When the ibudilast is orally administered to human in a dosage form having no substantial release, a rapid absorption from alimentary tract will produce a steep rise of serum concentration, resulting in side-effects such as nausea and vomiting. Therefore, as far as oral drugs are concerned, sustained release capsules, tablets and the like are proposed for the compound (Japanese Laid-Open Patent Application Sho 60-193913, corresponding to EP-A-0 156 243). Also the compound has been successfully prepared for rectal administration because of finding out bases for preventing a rapid increase in the serum concentration (Japanese Laid-Open Patent Application Sho 60-193913).

Since bronchial asthma and cerebrovascular disorder are often found among children and senile patients, respectively, it has been strongly desired that the development of a dosage form of ibudilast which is more easily administered.

SUMMARY OF THE INVENTION

The present inventors have been extensively studied about the dosage form which assures easy administration and excellent sustained release or long acting property. As the result of studies it has been found that ibudilast is excellent in transdermal absorption and have eventually invented a transdermal absorptive drug formulation containing ibudilast as effective constituent with reduced side-effects, such as vomitting and the like.

This transdermal absorptive drug formulation may be utilized in the dosage form such as ointment, cream, plaster or the like.

DETAILED DESCRIPTION OF THE INVENTION

As for the bases for ointments or cream, oily base, water-soluble base, suspending base, oil-in-water type emulsion base and water-in-oil type emulsion base will be employed. The ointment of ibudilast may be prepared by the use of any of these bases, however, as a base having excellent absorptive and long acting properties, the water-in-oil type emulsion base is particularly preferable.

For preparing the ointment, 1 to 10 wt% of ibudilast is blended with the ointment base, if necessary heated to obtain a homogeneous mixture and then solidified to obtain said drug.

The plaster is applied in the dosage forms of patch, cataplasm, transdermal patch, adhesive tape and the like. For preparing the plaster of ibudilast, it is preferable that an ointment base is blended with ibudilast or applied on a cloth to be formed together with other constituent materials such as substrates, liners, backing materials. The ibudilast concentration in the plaster ranges from 0.5 to 10 $mg/cm^2$, preferably 1 to 5 $mg/cm^2$.

For the purpose of controlling the drug release from the plaster, a method may be employed wherein a drug releasing layer is formed between the drug storing layer and the adhesive mass as well as the ingredients of the plaster are modified.

Thus obtained transdermal absorptive drug formulation of ibudilast according to this invention, excellent in its absorption property, may be employed under any condition of a disease such as that in asthma fit or the like, and can be conveniently applied, with remarkably reduced side-effects such as nausea, vomitting and the like. Also, the dosage form itself can freely control the dose amount, and as plaster, the drug has many advantages such as prevention of the contamination of clothes by the ointment base or the drug.

DETAILED DESCRIPTION OF THE PREFERRED EMBODIMENTS

EXAMPLE

The following examples illustrate the referred embodiments of this invention, but are not intended to limit its scope.

Example 1

After mixing 47.5 g of liquid paraffin with 47.5 g of white vaseline, the mixture was heated to about 60° C. to be dissolved. 5 g of ibudilast is added to the solution and dissolved. Then the resultant solution was cooled to room temperatures under stirring to produce an oily ointment.

Example 2

47.5 g of macrogol-4000 and 47.5 g of macrogol-400 were mixed together homogeneously, then 5 g of ibudilast was added to the mixture and mixed to produce a macrogol ointment.

Example 3

23.75 g of white vaseline, 19 g of stearyl alcohol, 3.8 g of polyoxyethylene hydrogenated castor oil-60, 0.9 g of glycerol monostearate and 5 g of ibudilast were mixed together, and the mixture was kept at 75° C. under stirring. Separately, 0.095 g of methyl p-hydroxybenzoate and 0.095 g of propyl p-hydroxybenzoate were dissolved into 11.4 g of propylene glycol, and 360 g of purified water was added to the solution, then the mixture was heated to 75° C. Then this solution was added to the former solution and stirred to form a latex. The latex was cooled and mixed until it became solidified to produce a hydrophilic ointment.

Example 4

Taking 380 g of white vaseline, 95 g of cetanol, 47.5 g of mustard beeswax, 47.5 g of sorbitan sesquioleate, 4.75 g of macrogol and 50 g of ibudilast, they were melted together by heating and kept at 75° C. To this solution were added a previously prepared solution which was produced by adding 0.95 g of methyl p-hydroxybenzoate and 0.95 g of butyl p-hydroxybenzoate into about 374 ml of purified water and heated the mixture at 80° C. The resultant mixture was blended to make a latex, then it was cooled and mixed until it became solidified to form a absorptive ointment.

Example 5

25 g of stearyl alcohol, 5 g of stearic acid, 5 g of polyethylene glycol-6000, and 5 g of 1,2,6-hexanetriol, were dissolved together by heating at 80° to 85° C. then into which 5.3 g of ibudilast was added and mixed. To this solution was added 60 g of separately prepared propylene glycol warmed at 90° C. and stirred. Then, the resultant mixture were stirred and cooled until it became solidified to obtain a FAPG ointment.

Example 6

Into 20 g of purified water, 1 g of Carboball-934 was added and was allowed to be swollen, to which was added a solution made by mixing 12 g of propylene glycol, 30 g of ethanol, 2 g of di-isopropyl adipate and 5.3 g of ibudilast. Then was added to the mixture a solution which was independently prepared by dissolving 1.1 g of di-isopropanolamine into 10 ml of purified water. And another 23.9 g of purified water was added to the solution and stirred homogeneously to form a gell ointment.

Example 7

5 g of ibudilast was dissolved into a 100 ml of silicone adhesive mass solution. The resulting liquid was applied to a non-rigid PVC sheet and dried at 60° C. for 30 min. to produce a plaster preparation.

Test 1

Transdermal absorptive drug formulations which were prepared according to the foregoing examples were measured to determine transdermal absorption ratios.

The test procedures were as follows: after shaving the back of about 3 kg of a albino rabbit with a hair-cutter, each of the ointments prepared according to the methods shown in the foregoing examples was applied in an amount of 1.5 g onto said shaved skin surface, and after the elapse of 5 hours after the application of ointment, it was recovered to measure the residual amount of ibudilast and the absorption ratio thereof was calculated. Table 1 shows the results.

TABLE 1

| Absorption Ratios of Ibudilast of Ointments | | |
|---|---|---|
| Example | Type of Ointment | Absorption Ratio (%) |
| 1 | Oily Ointment | 17.3 |
| 2 | Macrogol Ointment | 3.5 |
| 4 | Absorptive Ointment | 42.6 |
| 5 | FAPG Ointment | 13.1 |

Transdermal absorption of ibudilast was recognized in any of the ointments. In particular, the absorptive ointment had a high value of transdermal absorption ratio.

Test 2

Measurement was conducted on the serum concentration due to the use of the transdermal absorptive ointments prepared according to the foregoing examples.

This test was conducted as follows: about 3 kg of a albino rabbit prepared, the hair of its back was shaved with a hair-cutter, and an ointment according to the example 4 was applied in an amount of 1.6 g (per one rabbit) to the rabbit; and after a predetermined time, the blood samples were prepared, from which serum was separated and subjected to high performance liquid chromatography to measure the serum concentrations of ibudilast. Table 2 shows the results.

TABLE 2

| | Serum Concentrations of Ibudilast in Rabbit | | | | |
|---|---|---|---|---|---|
| Drug | 1 hr | 2 hr | 3 hr | 4 hr | (ng/ml) 6 hr |
| Absorptive Ointment | 62 | 119 | 68 | 92 | 77 |

The serum concentration of ibudilast began to show a high value after the elapse of one hour after the application of the ointment and high values were kept for a long time, indicating its usefulness as a transdermal absorptive drug formulation.

As stated above, the transdermal absorptive drug formulations according to this invention abate side-effects such as nausea, vomitting and the like caused when the drug is orally administered and have effects to keep a high concentration in the blood for a long time.

What is claimed is:

1. A transdermal absorptive drug formulation containing an anti-bronchial asthma effective amount of 3-isobutyryl-2-isopropylpyrazolo[1,5-a]pyridine.

2. A transdermal absorptive drug formulation according to claim 1, wherein the transdermal absorptive drug formulation is in the form of an ointment.

3. A transdermal absorptive drug formulation according to claim 1, wherein the transdermal absorptive drug formulation is in the form of a plaster.

4. A transdermal absorptive drug formulation, according to claim 2, wherein the amount of 3-isobutyryl-2-isopropylpyrazolo[1,5-a]pyridine contained in said drug ranges from 1 to 10 wt %.

5. A transdermal absorptive drug formulation containing an anti-cerebrovascular disorder effective amount of 3-isobutyryl-2-isopropylpyrazolo[1,5-a]pyridine.

6. A transdermal absorptive drug formulation according to claim 5 wherein the transdermal absorptive drug formulation is in the form of an ointment.

7. A transdermal absorptive drug formulation according to claim 5 wherein the transdermal absorptive drug formulation is in the form of a plaster.

8. A transdermal absorptive drug formulation according to claim 3 wherein the amount of 3-isobutyryl-2isopropylpyrazolo-[1,5-a]pyridine contained in said drug ranges from 1 to 10 wt. %.

9. A method for treating bronchial asthma comprising administering an anti-bronchial asthma effective amount of 3-isobutyryl-2-isopropylpyrazolo[1,5-a]pyridine transdermally. isobutyryl-2-isopropyrazolo[1,5-a]pyridine effective amount of 3-isobutyryl-2-isopropylpyrazolo[1,5-a]pyridine transdermally.

10. A method for treating cerebrovascular disorder comprising aministering an anti-cerebrovascular disorder effective amount of 3-isobutyryl-2-isopropylpyrazolo[1,5-a]pyridine transdermally.

* * * * *